US 11,127,495 B2

(12) United States Patent
Trindade Rodrigues et al.

(10) Patent No.: US 11,127,495 B2
(45) Date of Patent: Sep. 21, 2021

(54) QUALITY MANAGEMENT OF IMAGING WORKFLOWS (71) Applicant: KONINKLIJKE PHILIPS N.V., Eindhoven (NL)

(72) Inventors: Andreia Maria Araujo Trindade Rodrigues, Veldhoven (NL); Pedro Jorge Da Silva Rodrigues, Veldhoven (NL); Amy Perkins, Philadelphia, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 454 days.

(21) Appl. No.: 15/779,571

(22) PCT Filed: Dec. 7, 2016

(86) PCT No.: PCT/EP2016/080049
§ 371 (c)(1),
(2) Date: May 29, 2018

(87) PCT Pub. No.: WO2017/097825
PCT Pub. Date: Jun. 15, 2017

(65) Prior Publication Data
US 2020/0303059 A1    Sep. 24, 2020

Related U.S. Application Data (60) Provisional application No. 62/264,357, filed on Dec. 8, 2015.

(51) Int. Cl.
*G16H 40/20* (2018.01)
*G16H 30/20* (2018.01)
(Continued)

(52) U.S. Cl.
CPC .......... *G16H 40/20* (2018.01); *G06F 3/0481* (2013.01); *G06T 7/0012* (2013.01); *G16H 30/20* (2018.01); *G16H 50/30* (2018.01)

(58) Field of Classification Search
CPC .......... G06F 19/00; G06F 19/32; G06F 17/18; G06F 19/30; G06Q 50/22; G06Q 50/24;
(Continued)

(56) References Cited

U.S. PATENT DOCUMENTS

2006/0282302 A1   12/2006  Hussain
2011/0201900 A1*   8/2011  Zhang ................ G16H 15/00
                                                      600/300
(Continued)

FOREIGN PATENT DOCUMENTS

JP    2007316753 A    12/2007
JP    2012022552 A     2/2012

OTHER PUBLICATIONS

Noel, Camille E, et al: "Process-based quality management for clinical implementation of adaptive radiotherapy", Medical Physics, AIP, Melville, NY, US, vol. 41, No. 8, Jul. 30, 2014 (Jul. 30, 2014) (Year: 2014).*

(Continued)

Primary Examiner — Joseph D Burgess (57) ABSTRACT

A method includes identifying an imaging workflow process and constructing and displaying, in a graphical user interface, a graphical process tree for the imaging workflow process and a plurality of steps thereof. The method further includes identifying a standard of interest and mapping the plurality of steps into the standard of interest in the displayed graphical process tree. The method further includes receiving, via the graphical user interface, an input indicating a potential failure mode information for two or more of the steps, calculating at least one risk priority number for each step, evaluating the numeric assessment of risk based on a (Continued)

risk priority number threshold, and visually highlighting displayed steps corresponding to steps with risk priority numbers that exceed the risk priority number threshold. The method further includes determining a risk management plan to mitigate risk based on the highlighted steps.

20 Claims, 8 Drawing Sheets (51) Int. Cl.
    *G16H 50/30* (2018.01)
    *G06F 3/0481* (2013.01)
    *G06T 7/00* (2017.01)

(58) Field of Classification Search
    CPC .............. G06Q 10/06; G06Q 10/0633; G06Q 10/06395; G16H 50/20; G16H 10/60; G16H 15/00; G16H 40/20; G16H 40/63; G16H 80/00; G16H 30/20; G16H 30/40; G16H 40/67; G16H 70/20; G16H 20/40
    See application file for complete search history.

(56) References Cited

U.S. PATENT DOCUMENTS

| 2016/0000401 | A1* | 1/2016 | Mienkina | A61B 8/5223 |
| | | | | 600/443 |
| 2016/0140300 | A1* | 5/2016 | Purdie | A61N 5/103 |
| | | | | 705/2 |
| 2018/0052962 | A1* | 2/2018 | Van Der Koijk | G16H 70/20 |

OTHER PUBLICATIONS

Catelani, M, et al: "ISO 14971 as a methodological tool in the validation process of a RIS-PACS system", Medical Measurements and Applications Proceedings (MEMEA), 2011 IEEE International Workshop on, IEEE, May 30, 2011 (May 30, 2011), pp. 408-412 (Year: 2011).*

"Application of failure mode and effects analysis (FMEA) to pretreatment phases in tomotherapy", Journal of Applied Clinical Medical Physics, vol. 14, No. 5, 2013, Broggi, Sara, et at. (Year: 2013).*

Younge, Kelly Cooper, et al: "Practical Implementation of Failure Mode and Effects Analysis for Safety and Efficiency in Stereotactic Radiosurgery", International Journal of Radiation: Oncology Biology Physics, vol. 91, No. 5, Apr. 1, 2015 (Apr. 1, 2015), pp. 1003-1008 (Year: 2015).*

Cooper, et al., "Practical Implementation of Failure Mode and Effects Analysis for Safety and Efficiency in Stereotact Radiosurgery"; International Journal of Radiation: Oncology Biology Physics, vol. 91, No. 5, Apr. 1, 2015.

Catelani, et al., "ISO 14971 as a methodological tool in the validation process of a RIS-PACS system" Medical Measurements and Applications Proceedings (MEMEA), 2011 IEEE.

Manger, et al., "Failure mode and effects analysis and fault tree analysis of surface image guided cranial radiosurgery" Medical Physics, vol. 42, No. 5, May 1, 2015.

Noel, et al., "Process-based quality management for clinical implementation of adaptive radiotherapy"; Medical Physics, vol. 41, No. 8, Jul. 30, 2014.

"Healthcare Failure Mode and Effect Analysis (HFMEA)", VA National Center for Patient Safety, http://www.patientsafety.va.gov/professionals/onthejob/hfmea.asp.

Kapur et al, "Six sigma tools for a patient safety-oriented, quality-checklist driven radiation medicine department" in Practical Radiation Oncology, 2012, vol. 2, pp. 86-96.

Porter, et al., "The Strategy that Will Fix Health Care", Harvard Business Review, 51-70, Oct. 2013.

RSNA, "FDG-PET/CT as an Imaging Biomarker Measuring Response to Cancer Therapy, Quantitative Imaging Biomarkers Alliance", FDG-PET/CT Technical Committee, Version 1.05, Publicly Reviewed Version. QIBA, Dec. 11, 2013.

Taner et al, "Application of Six Sigma methodology to a diagnostic imaging process"; International Journal of Health Care Quality Assurance, vol. 25, No. 4, 2012, pp. 274-290.

Johnson et al, "Process Improvement: What Is It, Why Is It Important, and How Is It Done?" in American Journal of Roentgenology, Feb. 2010, vol. 194, No. 2, pp. 461-468.

* cited by examiner

QUALITY MANAGEMENT OF IMAGING WORKFLOWS

CROSS REFERENCE TO RELATED APPLICATIONS

This application is the U.S. National Phase application under 35 U.S.C. § 371 of International Application No. PCT/EP2016/080049, filed Dec. 7, 2016, published as WO 2017/097825 on Jun. 15, 2017, which claims the benefit of U.S. Provisional Patent Application No. 62/264,357 filed Dec. 8, 2015. These applications are hereby incorporated by reference herein.

FIELD OF THE INVENTION

The following generally relates to imaging workflow management and more particularly to process-based quality management of imaging workflows for imaging modalities such as positron emission tomography (PET), computed tomography (CT), single photon emission tomography (SPECT), magnetic resonance imaging (MRI), a combination thereof, and/or other imaging modality(s).

BACKGROUND OF THE INVENTION

Positron Emission Tomography (PET) is a medical imaging modality that allows extracting quantitative information about bio distribution of metabolic active contrast agents, e.g. fluorodeoxyglucose (FDG), fluoroethyltyrosine (FET), fluorothymidine (FLT), fluoromisonidazole (FMISO), etc. PET not only allows representing visually the distribution of administered, metabolically active radiopharmaceuticals, but it also provides quantification of how much of the radiopharmaceutical has accumulated within a specific region. For instance, administrating FDG (a glucose analogue) allows quantifying the cell inwards glucose transport, as FDG is trapped inside the cells. Tumor cells are highly metabolically active and uptake and retain higher levels of FDG when compared to normal tissues.

With PET it is possible to tell exactly how many decays from the radio isotope were counted in the specific region, thus one can compare these numbers to previous or later PET scans and evaluate if the uptake and retention has remained stable, decreased or increased. This evaluation is of utmost importance for evaluation if a disease responds to a therapy, especially in oncology. For practical ease, Standard Uptake Values (SUV) are computed in clinical routine instead of directly using decay counts. The SUV is used for quantifying the relative average activity and the relative maximum activity of lesions. A correct computation of SUV values is especially important for evaluation of tumors to therapy.

Several evaluation criteria exist, (Response Evaluation Criteria in Solid Tumors (RECIST), PET RECIST (PERCIST), European Organization for Research and Treatment of Cancer (EORTC), World Health Organization (WHO)). The evaluation criteria PERCIST and EORTC evaluate the SUV values in treated tumors. These schemes indicate how to interpret quantitative PET images for deciding if a cancer responds to a therapy or not, e.g. the EORTC criteria recommends to classify a cancer disease as progressive if the SUV increases by more than 15% from one PET scan to a second one. An improved computation of SUV values thus leads to improved evaluation of the disease. SUVs are now routinely reported, and are asked for the different clinical actors in the diagnostic and treatment pathway, from the clinically proven detection up to the longitudinal follow-up stage.

The accuracy of the SUV values is connected to the selected PET imaging workflow. In similar manner, the same dependency between the quantitative data and the selected workflow is observed in other modalities like in dynamic contrast-enhanced MRI (DCE-MRI). In the case of PET, different protocols have been set. The Uniform Protocol for Imaging in Clinical Trials (UPICT) protocol establishes a hierarchy with tiered levels of protocol compliance. This reflects the recognition that there are valid reasons to perform trials using different levels of rigor, even for the same disease/intervention combination. For example, a high level of image measurement precision may be needed in small, early-phase trials, whereas a less rigorous level of precision may be acceptable in large, late-phase trials of the same drug in the same disease setting. This protocol defines acceptable (minimum) target and ideal standards for all phases of the imaging workflow Medical imaging faces challenges to improve efficacy and reduce costs. In this view, significant changes will be required for how health care delivery is organized, measured and reimbursed. Providers will need to be able to show how improvements in outcomes and efficiency are met and how they compare with other providers. Providers will be required to report compliance with guidelines and, as such, implement quality auditing policies. However, the multiple parameters in the different workflow phases that are needed to address the practical implementation of such recommendations can be daunting and time-consuming. Furthermore, each clinic is different and the critical paths to the implementation of a workflow can easily vary. Moreover, there is a need to assist the providers to develop their own specific process map in order to identify potential error pathways. Unfortunately, there is no guidance on how to develop and implement a quality management system to achieve a defined level of quality of a specific imaging workflow.

SUMMARY OF THE INVENTION

Aspects of the present application address the above-referenced matters and others.

According to one aspect, a method includes identifying an imaging workflow process of interest and constructing a graphical process tree for the imaging workflow process of interest. The imaging workflow process includes a plurality of steps, and the graphical process tree includes the plurality of steps. The method further includes visually displaying the graphical process tree and the steps in a graphical user interface, identifying a protocol specific workflow standard of interest, mapping the plurality of steps into the protocol specific workflow standard of interest, and visually displaying the graphical process tree with the steps mapped into the standard in the graphical user interface. The method further includes receiving, via the graphical user interface, an input indicating a potential failure mode information for two or more of the steps, calculating at least one risk priority number (RPN) for each step, evaluating the numeric assessment of risk based on a risk priority number threshold, and visually highlighting displayed steps corresponding to steps with risk priority numbers that exceed the risk priority number threshold. The method further includes determining a risk management plan to mitigate risk based on the highlighted steps.

In another aspect, a computing system includes a memory device configured to store instructions, including a record integration module, and processor configured to executes the instructions. The processor, in response to executing the instructions: process image examination information for failure mode information, wherein the image examination information includes image examination information for scans performed after implementation of a risk management plan for an imaging workflow process having a plurality of steps, calculate at least one risk metric for each step based on the failure mode information, evaluate the risk metric based on risk criteria, visually identify steps of the plurality of steps that satisfy the risk criteria, and update the risk management plan to mitigate risk based on the steps identified as satisfying the risk criteria.

In another aspect, a non-transitory computer readable medium is encoded with computer executable instructions, which, when executed by a processor of a computer, cause the computer to: construct a graphical process tree, for an imaging workflow process, with branches that correspond to steps for completing the imaging workflow process, wherein at least a sub-set of the steps are mapped into a protocol specific workflow standard of interest, calculate at least one risk priority number for each step based on input corresponding to potential failure modes, process each risk priority numbers based on a risk priority number threshold, identify steps having risk priority numbers that exceed the risk priority number threshold, determine a risk management plan to mitigate risk based on the identified steps, update the at least one risk priority number based on image examination failures after implementing the risk management plan, and update the risk management plan to mitigate risk based on the updated at least one risk priority number.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
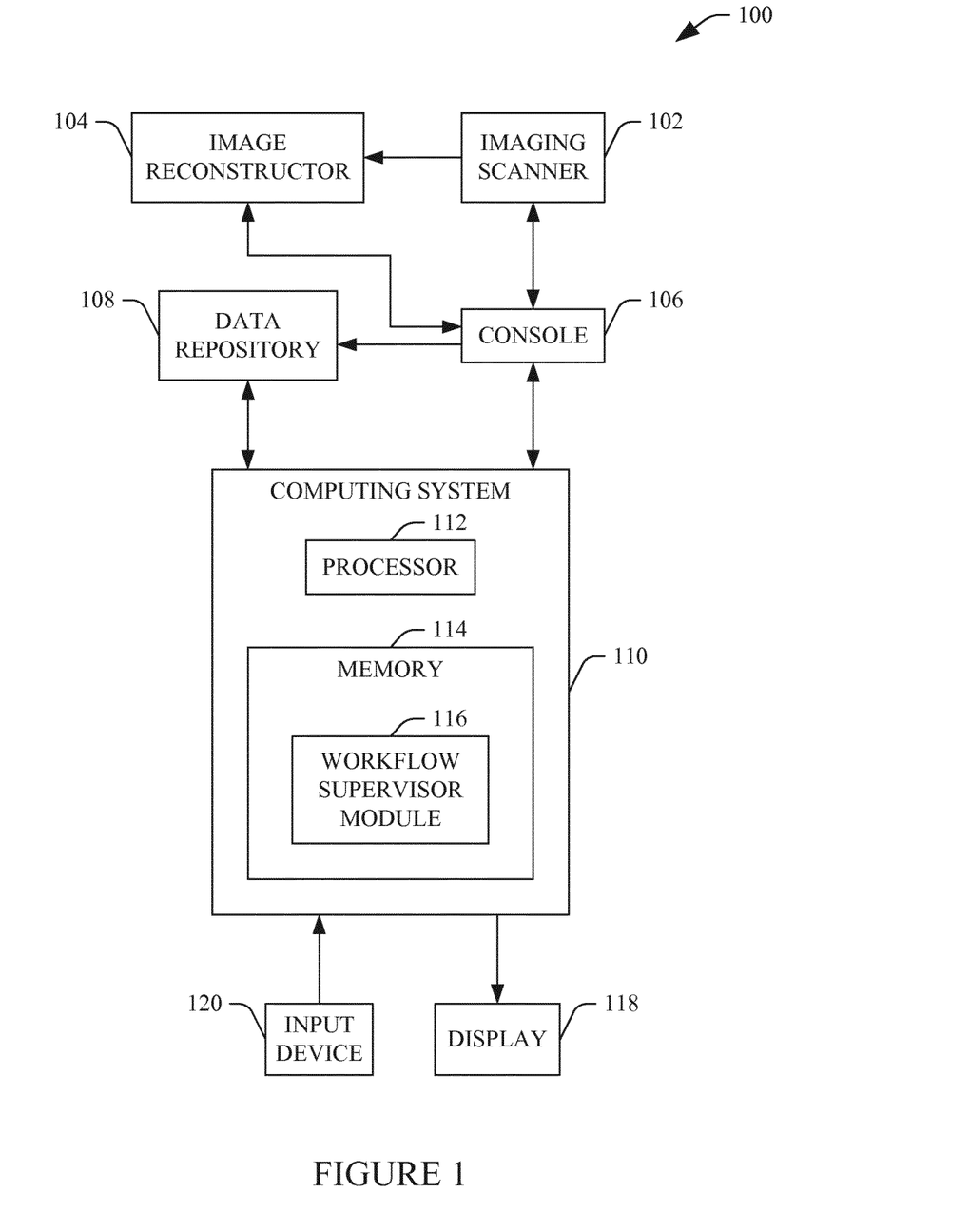
FIG. 1 schematically illustrates an example system with a computing device configured to execute a workflow supervisor module.

FIG. 1 illustrates a system 100. The system 100 includes an imaging scanner 102. Examples of suitable scanners include a positron emission tomography (PET), computed tomography (CT), single photon emission tomography (SPECT), magnetic resonance imaging (MRI), a combination thereof and/or other imaging scanner. The imaging scanner 102 is configured with a suitable acquisition system (e.g., a detector/sensor, etc.) based on the particular imaging modality. The acquisition system generates and outputs data indicative of a scanned object or subject.

An image reconstructor 104 processes the output data and generates one or more structural and/or functional images of the scanned object or subject. A console 106 is configured to control the imaging scanner 102 and/or the image reconstructor 104. A data repository 108 stores examination data such as the images generated by the image reconstructor 104. Examples of a suitable data repository 108 include a picture archiving and communication system (PACS), a radiology information system (RIS), a hospital information system (HIS), an electronic medical record (EMR), and/or other data repository. The data repository 108 also stores user identified imaging procedure failure modes for examination data stored therein.

The system 100 further includes a computing system 110. The computing system 110 includes at least one processor 112 (e.g., a microprocessor, a central processing unit, etc.) that executes at least one computer readable instruction stored in a computer readable storage medium ("memory") 114, which excludes transitory medium and includes physical memory and/or other non-transitory medium. The at least one computer readable instruction, in this example, includes a workflow supervisor module 116 with corresponding computer executable instructions. The computing system 110 includes output device(s) 118, such as a display monitor, portable memory, a network interface, etc., and an input device(s) 120 such as a mouse, keyboard, a network interface, etc.

The instructions of the workflow supervisor module 116, when executed by the at least one processor 112, cause the at least one processor 112 to identify, for a particular individual healthcare institution, errors that can impair the application of an imaging protocol and suggest the implementation of a risk-mitigation plan with risk-mitigation strategies. As described in greater detail below, this is achieved through an interactive graphical user interface (GUI), which graphically presents a workflow process in a tree format, maps steps of the workflow into a standard, processes risk information for one or more steps, identifies errors that lead to the implementation of risk-mitigation strategies, and updates the identification by analyzing risk from the outcome of examinations performed after implementation of the risk-mitigation strategies. As such, the approach described herein can assist the implementation of quality auditing imaging workflows with respect to a particular standard and point to additional quality controls.

Figure 2:
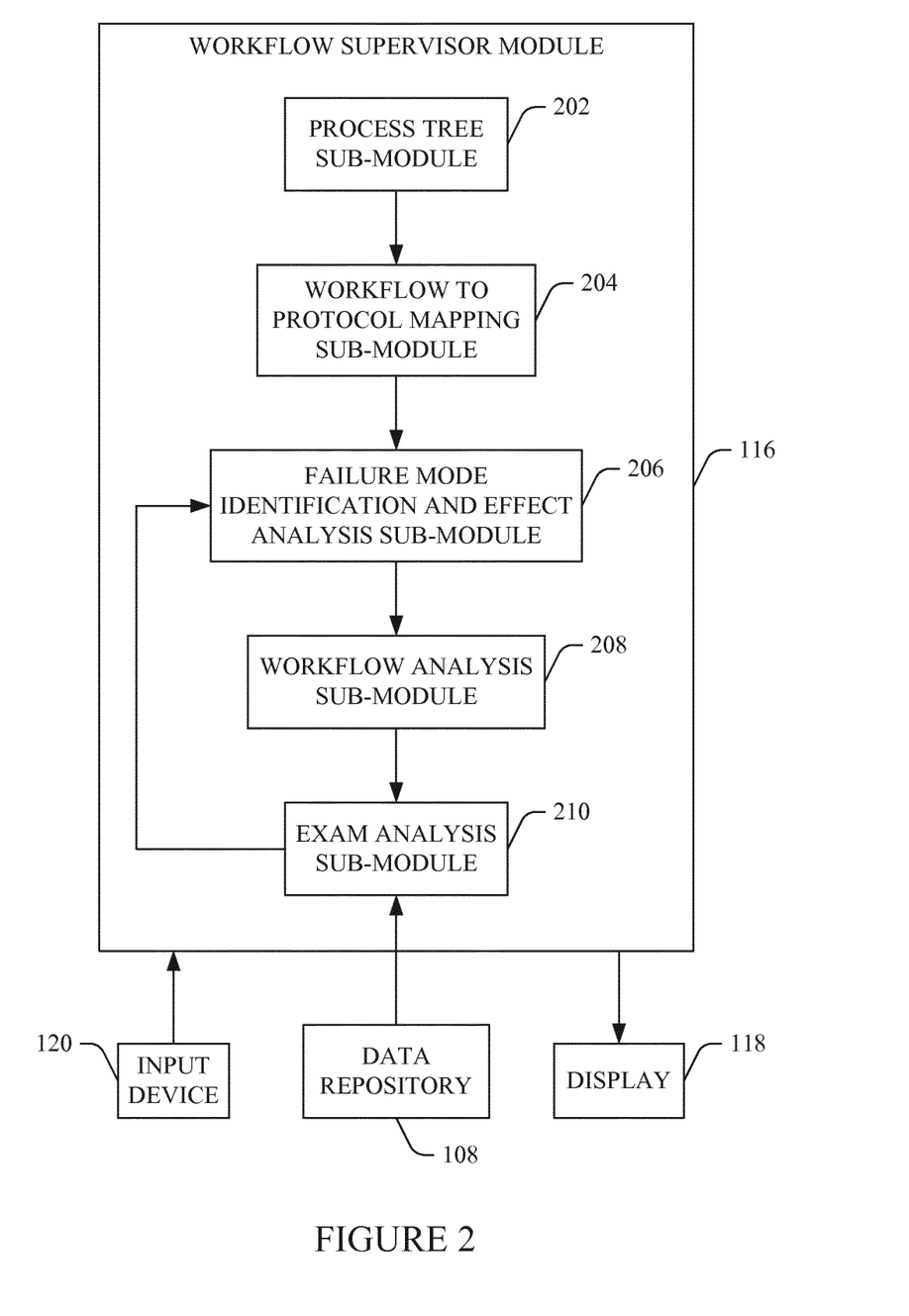
FIG. 2 schematically illustrates example sub-modules of the workflow supervisor module.

FIG. 2 schematically illustrates an example of the workflow supervisor module 116. The illustrated workflow supervisor module 116 includes a plurality of sub-modules, including a process tree sub-module 202, a workflow to protocol mapping sub-module 204, a failure mode identification and effect analysis sub-module 206, a workflow analysis sub-module 208, and an exam analysis sub-module 210. In general, the workflow supervisor module 116, after performing an initial risk assessment based on user input to identify risk-mitigation strategies, updates the assessment based on an outcome of examinations after implementing the risk-mitigation strategies. In other embodiments, the module 116 can include more, less, similar, different, etc. sub-modules.

The workflow supervisor module 116 of FIG. 2 is based on a process-based framework in which a Design for Reliability (DfR) approach, e.g., Failure Mode Error Analysis (FMEA), enables the identification and comparison of process-specific risks. The update loop updates risk areas on-the-fly by continuously adding the clinical experience, improving the initial FMEA-type analysis that relies on a human consensus or expert opinion. The update loop can also reflect the impact in the workflow due to introduction of new tools and resources in the service. This data-driven analysis re-iterates estimates to provide a more quantitative assessment of risks. In other embodiment, the workflow supervisor module 116 is based another framework(s).

The process tree sub-module 202 implements a process-based analysis of the implemented workflow, constructing a graphical process tree. The workflow to protocol mapping sub-module 204 maps steps of the workflow process tree into guidelines of a specific standard or profile. A set of potential failures, as defined by such protocol, is used as input. The failure mode identification and effect analysis sub-module 206 enables a clinical team (doctor, radiologist, and technologist) to assign and review, based on their experience, a likeliness of occurrence (O), outcome of severity in terms of the imaging task (S) and likeliness of failure being detected (D). Here likeliness of occurrence (O), outcome (S) and detectability (D) are defined within a FMEA formalism, but equivalent approaches can be derived based on other risk analysis and mitigation techniques.

The analysis sub-module 208 calculates a risk priority number (RPN) value and reports RPNs above a predefined threshold. The clinical team provides information on the particular imaging workflow, and the workflow is analyzed, and high-critical risks are highlighted. Risks present in the standard/profile but not captured in the initial workflow are identified and aid implementation of risk mitigation strategies and revised quality control. For each patient exam, a post-exam risk analysis value is computed. The exam analysis sub-module 210 employs this value to re-iterate the original RPNs values and derive updated workflow recommendations.

Figure 6:
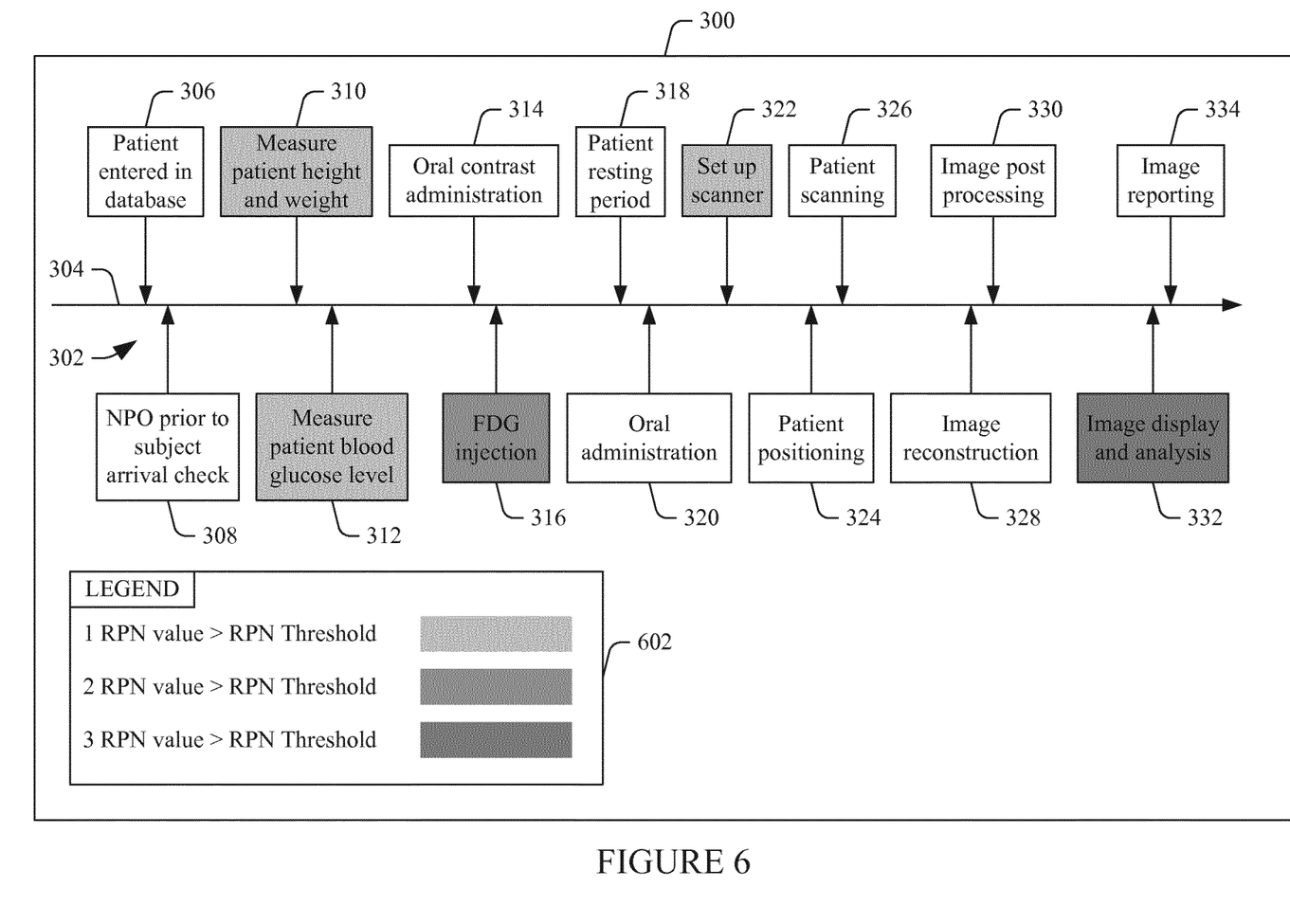
FIG. 6 schematically illustrates the GUI with the workflow process tree with RPNs for the process steps.
Figure 7:
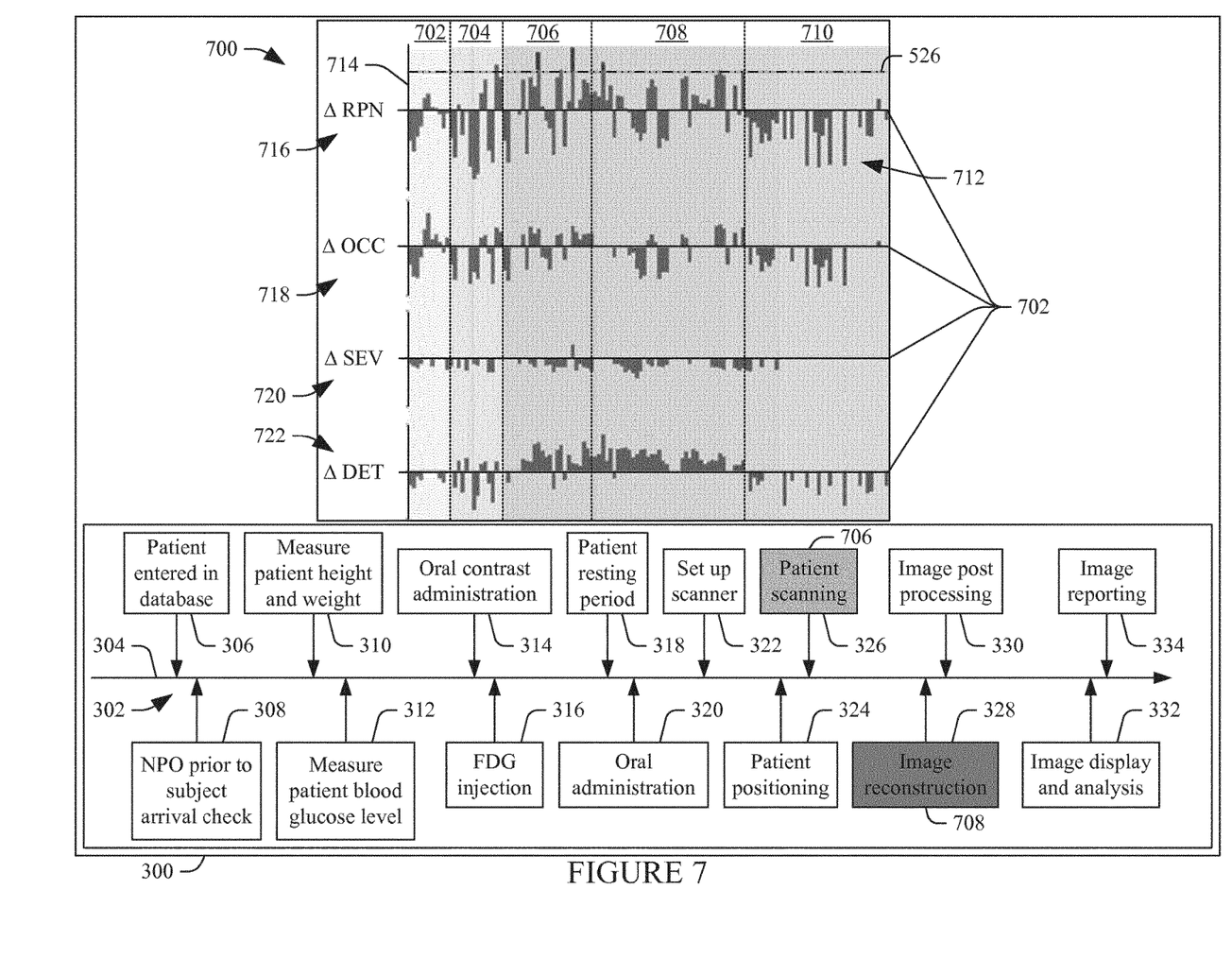
FIG. 7 schematically illustrates the GUI with the workflow process tree updated to reflect failures after quality strategies are identified and implemented.
Figure 8:
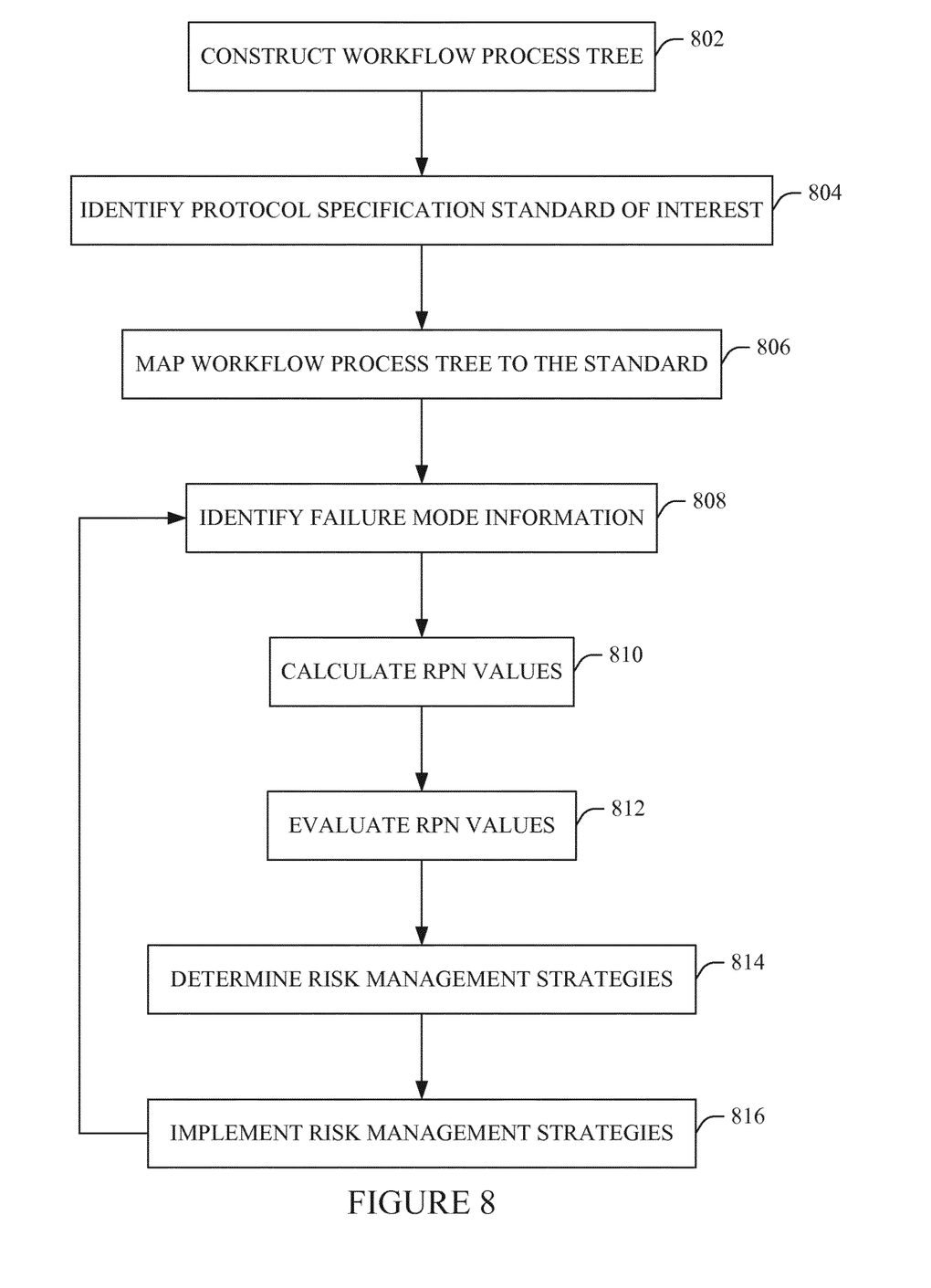
FIG. 8 illustrates an example method according to an embodiment herein.

An imaging workflow use-case scenario is described in connection with FIGS. 3-8. FIGS. 3-7 show screen shots of the interactive GUI for each of the sub-modules 202 to 210. FIG. 8 describes a method of using the workflow supervisor module 116, referencing the screen shots of FIGS. 3-7. In this example, the imaging workflow is a nuclear medicine (NM) 18F-FDG PET imaging workflow for oncology.

Figure 3:
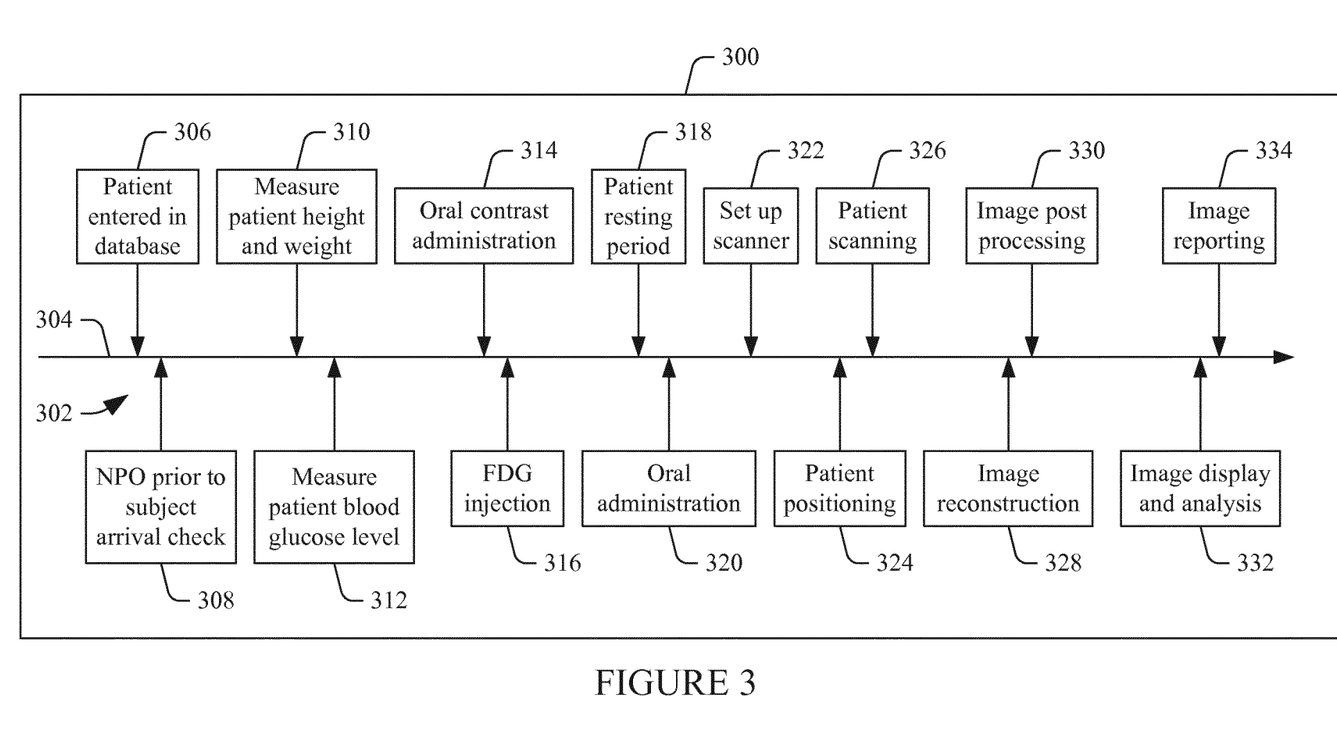
FIG. 3 schematically illustrates a GUI with an example workflow process tree.

Initially referring to FIG. 8, a workflow process tree for the PET imaging workflow is constructed and visually presented. FIG. 3 shows a graphical use interface (GUI) 300 with a PET workflow process tree 302. The process tree sub-module 202 (FIG. 2) creates the tree 302, which describes the temporal (from left to right) and physical relationships between the steps of the PET imaging workflow. A main process stream 304 runs down a middle of the tree 302, forming a trunk of the tree 302. From the trunk 304 are branches for the steps that are acquired to execute the PET imaging procedure. The details of the tree 302 may vary from institution to institution, and may include more, less, different, etc. steps for each institution.

The illustrated steps include a patient entered in database step 306, a NPO (nil per os, or nothing by mouth) prior to subject arrival check step 308, a measure patient height and weight step 310, a measure patient blood glucose level step 312, an oral contrast administration step 314, an FDG administration step 316, a patient resting period step 318, a second oral administration step 320, a set up scanner step 322, a patient positioning step 324, a patient scanning step 326, an image reconstruction step 328, an image post processing step 330, an image display and analysis step 332, and an image reporting step 334. Again, these steps may vary from institution to institution, and may include more, less, different, etc. steps.

Figure 4:
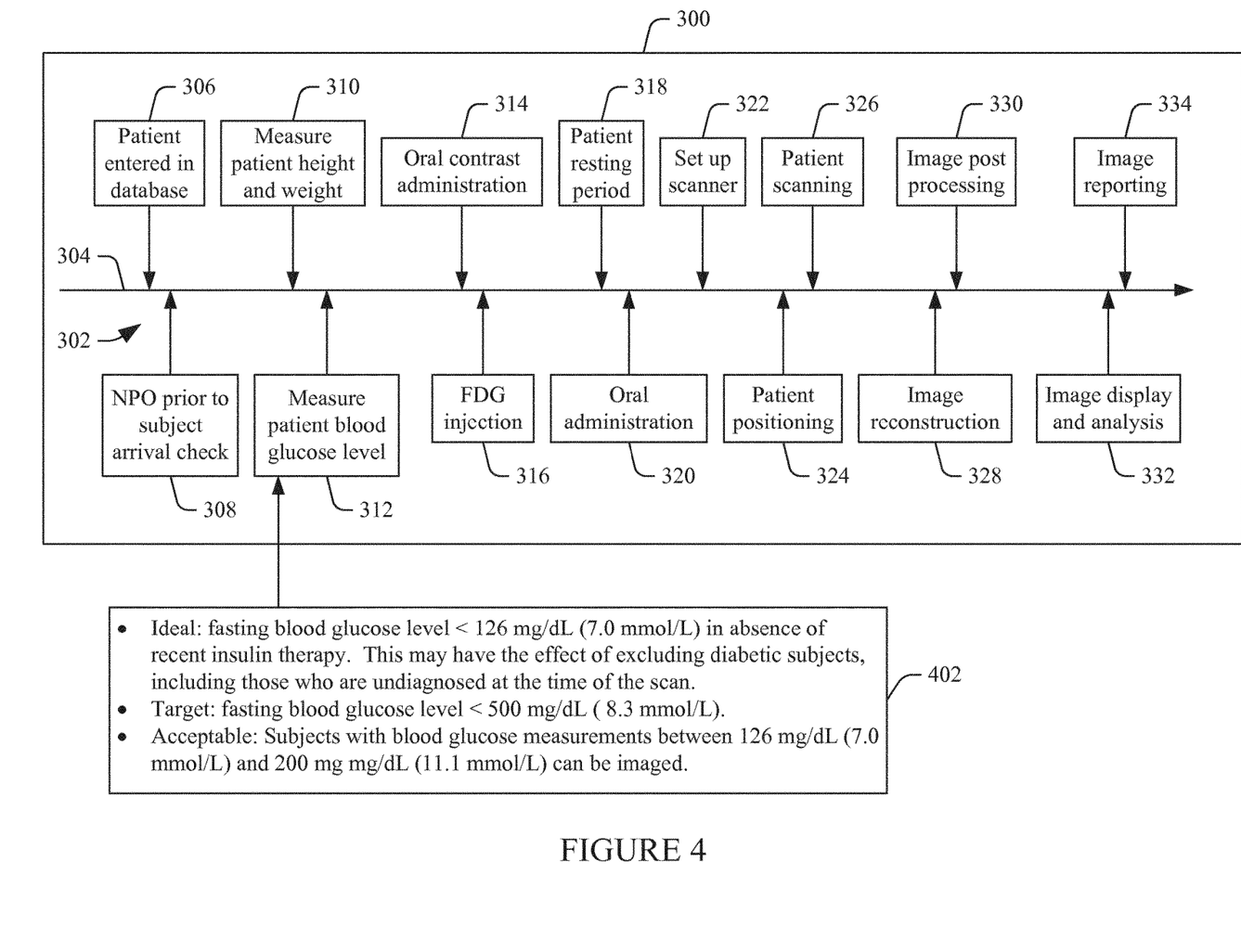
FIG. 4 schematically illustrates the GUI with the workflow process tree with a process step thereof mapped to a standard of interest.

Returning to FIG. 8, a standard or imaging protocol is identified at 804, and the steps of the process tree 302 are mapped into the standard at 806. The standard can be identified from a default, a user preference, etc., a user input, and/or other manner. FIG. 4 shows the graphical use interface (GUI) 300 with the tree 302 for the PET imaging workflow mapped, in part, to a particular standard. The workflow to protocol mapping sub-module 204 (FIG. 2) does this by assigning a correspondence between the different steps of the PET imaging workflow present in the tree 302 into the particular standard. FIG. 4 shows risk mapping between the measure patient blood glucose level step 312 and a Quantitative Imaging Biomarkers Alliance (QIBA) profile/UPICT protocol 402, in the context of oncology $^{18}$F-FDG PET.

Figure 5:
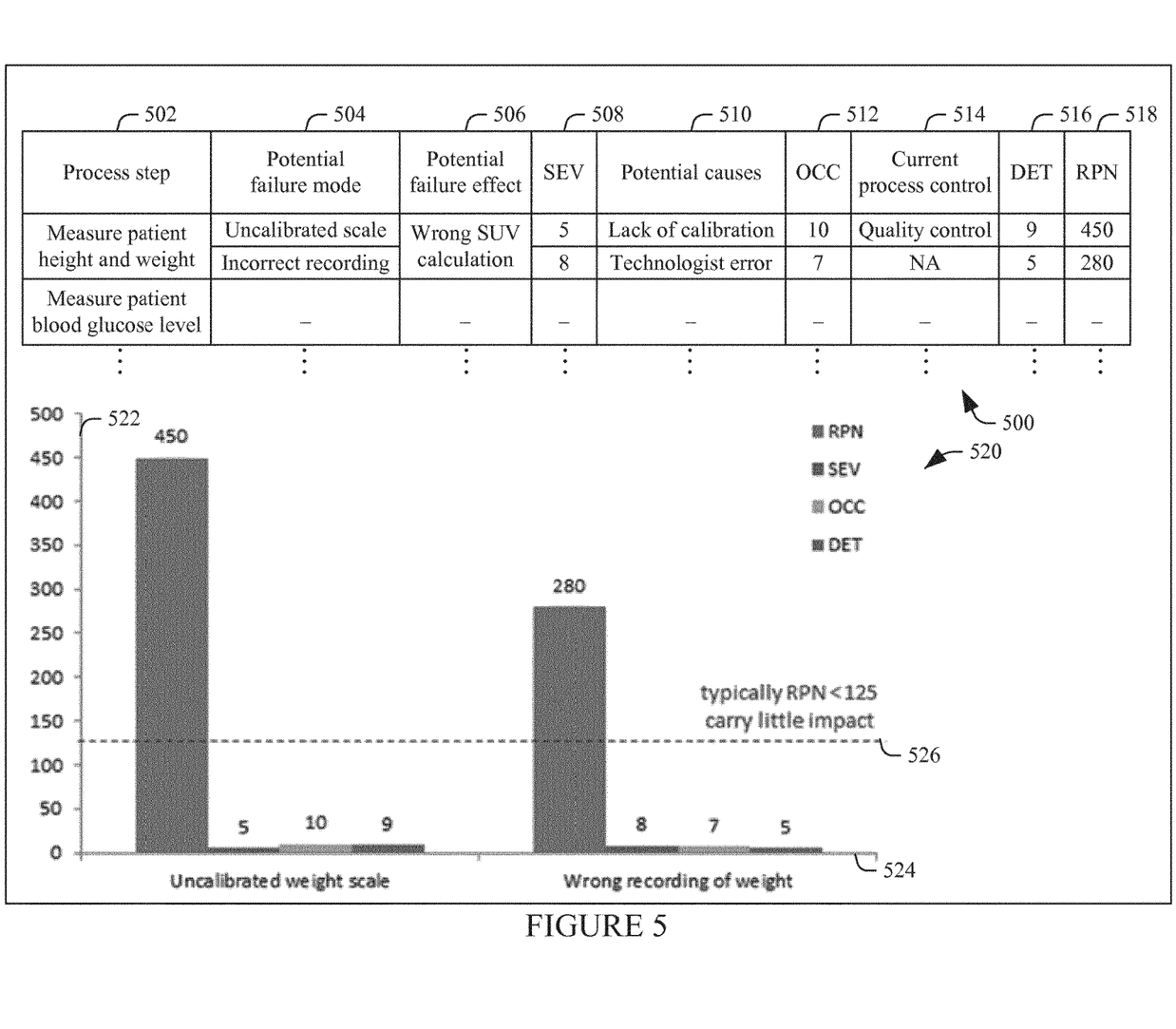
FIG. 5 schematically illustrates the GUI with an interactive Failure Modes and Effects Analysis ("FMEA") tool.

Returning to FIG. 8, failure mode information is identified at 808, and RPN values are calculated at 810. FIG. 5 shows the graphical use interface (GUI) 300 with a failure mode identification table 500 and an effect analysis graph 520. The failure mode identification and effect analysis sub-module 206 (FIG. 2) populates the table 500 with the steps from the tree 302 (FIG. 2), processes entries into the cells of the table 500, and generates the effect analysis graph 520 based thereon. In this example, risk assessment is achieved by establishing a severity of a failure if not mitigated, a probability of occurrence of each failure, and a probability each failure will be undetected. With imaging protocols, this allows a user to evaluate each the severity, detectability, likeliness of occurrence of each failure mode following a FMEA-type protocol.

The illustrated table 500 includes multiple fields. A first field 502 indicates the processing step, a second field 504 indicates a potential failure mode, a third field 506 indicates a potential failure effect, a fourth field 508 indicates a severity (SEV), a fifth field 510 indicates a potential cause, a sixth field 512 indicates a likeliness of occurrence (OCC), a seventh field 514 indicates a current process control, an eight field 516 indicates a detectability (DET), and a ninth field 518 indicates a RPN index. The first field 502 is populated with the steps 306-334 (FIG. 3), For sake of brevity, the illustrated field is shown populated only with the processing steps 310 and 312. The fields 504-516 are populated by data entered through an input 120 (e.g., a keyboard). The field 518 is automatically populated based on the entered data. In this FNMA-type example, the field 518 (RPN) is the product of fields 508, 512 and 516 (i.e., SEV×OCC×DET).

The second field 504 indicates, for the step 310, uncalibrated scale and incorrect recording. The third field 506 indicates, for the failure modes 504, a wrong SUV calculation effect. The fifth field 510 indicates, respectively for the uncalibrated scale and the incorrect recording failures, lack of calibration and technologist error as the cause. The seventh field 514 indicates, respectively for the lack of calibration and the technologist error, quality control and none processes are in place. The fourth, sixth, eighth and ninth fields 508, 512, 516 and 518 are configured to receive numerical values. In this example, the fourth field 508 (severity) includes a "5" for uncalibrated scale and an "8" incorrect recording using a range from 1 (no appreciable impact to the clinical outcome of the imaging procedure) to 10 (catastrophic, the exam needs to be redone). The impact scale can be derived from the FMEA formalism, but others are also possible, as long the used formalism is reported in order to enable comparisons between different clinical sites. The sixth field 512 (occurrence) includes a "10" for uncalibrated scale and a "2" incorrect recording using a range from 1 (1 failure in $10^4$) to 10 (highly likely, <5% of the time)). The eighth field 516 (detectability) includes a "9" for uncalibrated scale and a "5" incorrect recording using a range from 1 (detected only <0.01% of the time) to 10 (undetected <20% of the time).

The graph 520 presents the information in the fields 508, 512, 516 and 518. In the graph 520, a first axis 522 represents the RPN value in the fields 508, 512, 516 and 518, and a second axis 524 represents the different fields 508, 512, 516 and 518 for the potential failure modes 504 for the process step 502 being evaluated. The graph 520 further shows an RPN threshold 526, which is used to identify failure modes of interest to quality, wherein a failure mode above the RPN threshold 526 is deemed a current mode of interest to quality. The RPN threshold 526 can be set based on a desired imaging standard, the particular facility, etc., and can vary from processing step to processing step. As an example in the context of the QIBA profiles for quantitative 18F-FDG PET imaging, the RPN threshold 526 can be used to identify risks that makes an exam lose its quantitative nature and become semi-quantitative or qualitative only type of results.

Returning to FIG. 8, the RPN values are evaluated at 812. FIG. 6 shows the GUI 300 displaying results from the RPN-driven workflow analysis performed by the workflow analysis sub-module 208 (FIG. 2). The results include the tree 302 from FIG. 3 with the processing steps having RPN values that exceed the RPN threshold 526 highlighted. In this example, the highlighting is based on a grayscale coloring. The processing steps 310, 312 and 322 are highlighted to indicate that each of these processing steps has one RPN value that exceeds the RPN threshold 526. The processing step 316 is highlighted to indicate that it has two RPN values that exceed the RPN threshold 526. The processing step 332 is highlighted to indicate that it has three RPN values that exceed the RPN threshold 526. A legend 602 defines the grayscale coding. The remaining processes do not have an RPN value that exceeds the RPN threshold 526.

Returning to FIG. 8, risk management strategies are determined based at least on the RPN values at 814, and the risk management strategies are implemented at 816. Acts 808-816 are repeated based on results of examinations after the implementation of the risk management strategies. FIG. 7 shows the GUI 300 displaying updated results from the RPN-driven workflow analysis performed by the workflow analysis sub-module 208 (FIG. 2). The updated results update the highlighting described in FIG. 6 based on imaging examinations performed with the quality control strategies in place. In general, once quality control strategies are in place, for each exam that is made under a validated workflow and for each imaging system of the facility, failures that are detected and/or suspected by the technologist/staff/clinician are recorded and stored in the data repository 108 and/or other storage device.

The exam analysis sub-module 210 (FIG. 2) continuously, periodically, on demand, etc. processes the recorded failures, updates the values in the SEV 508, OCC 512 and DET 516 fields, and re-computes the values in the RPN field 518 (FIG. 5), the highlighted tree 302 (FIG. 6), and a graph 700, and display an updated highlighted tree 302 and the graph 700. In the graph 700, a first axis 702 indicates individual RPNs for each of a sub-set of the steps 306-334. The sub-sets are identified as 702, 704, 706, 708 and 710, and only five of the steps 306-334 are illustrated in FIG. 7 for sake of clarity. For the sub-set 710, and each bar 712 on the axis 702 corresponds to one of the RPNs for the process. By way of example, with respect to FIG. 4, for the processing step measure patient height and weight 310 in the processing field 502, there would be a bar for uncalibrated scale and another bar for incorrect recording.

A second axis 714 shows a indicates a change in RPN 716, a change in OCC 718, a change in SEV 720 and a change in DET 722. Each change can be positive or negative, depending on whether the severity, occurrence, detectability and RPN increased or decreased. The graph 700 further includes the RPN threshold 526 in connection with a plot of the change in the RPN value 714. The patient exam analysis and RPN update sub-module 210 highlights RPN values that exceed the RPN threshold 526 in the graph 700. For example, in the illustrated example, bars 724, 726, 728 and 730 are highlighted. The bar 724 corresponds to the process represented by 706, and the bars 726, 728 and 730 correspond to the process represented by 708. The tree 302 is updated to reflect the process represented by 706 includes one step with an RPN value that exceeds the RPN threshold 526, and the process represented by 708 includes three steps with an RPN value that exceeds the RPN threshold 526, using the color coding of FIG. 6.

It is to be appreciated that the ordering of the acts in the methods described herein is not limiting. As such, other orderings are contemplated herein. In addition, one or more acts may be omitted and/or one or more additional acts may be included. Furthermore, the above may be implemented by way of computer readable instructions, which when executed by a computer processor(s), cause the processor(s) to carry out the described acts. In such a case, the instructions can be stored in a computer readable storage medium associated with or otherwise accessible to the relevant computer. Additionally or alternatively, one or more of the instructions can be carried by a carrier wave or signal.

Variations are discussed next.

In the above, accurate baseline descriptions of the failures in terms of O, S and D factors are available from the healthcare facility. In a variation, the baseline values are instead obtained from a third-party. The O, S and D factors are then updated during execution as described herein.

In another variation, initial O, S and D factors are not available, even from a third party. With this variation, the O, S and D factors are then updated after a sufficient number of patient baseline values are defined.

In another variation, an alternative approach to quantifying the probability of occurrence of a fault and quantification of risk is used. By way of non-limiting example, a Healthcare FMEA approach with a hazard score can be used instead of computing RPN values. An example of a Healthcare FMEA approach is discussed in "Healthcare Failure Mode and Effect Analysis (HFMEA)", VA National Center for Patient Safety, http://www.patientsafety.va.gov/professionals/onthejob/hfmea.asp.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method of managing quality control of an imaging workflow process, the method comprising:
    visually displaying a graphical process tree for an imaging workflow process in a graphical user interface, the graphical process tree including a plurality of steps corresponding to the imaging workflow process;
    mapping the plurality of steps into a pre-established standard imaging protocol or profile;
    visually displaying the graphical process tree with the plurality of steps mapped into the standard imaging protocol or profile in the graphical user interface;
    receiving, via the graphical user interface, an input indicating potential failure mode information for two or more steps of the plurality of steps;
    calculating at least one risk priority number for each step of the plurality of steps;
    evaluating a numeric assessment of risk based on a risk priority number threshold;
    visually highlighting steps of the visually displayed graphical process tree in the graphical user interface having risk priority numbers that exceed the risk priority number threshold;
    determining a risk management plan to mitigate risk associated with the highlighted steps;
    adjusting the imaging workflow process in accordance with the risk management plan; and
    performing imaging examinations of patients using the adjusted imaging workflow process.

2. The method of claim 1, further comprising:
    processing image examination information stored in a data repository for updated failure mode information, wherein the image examination information includes image examination information for scans performed after implementation of the risk management plan;
    re-calculating the at least one risk priority number for each step based on the updated failure mode information;
    evaluating the updated risk priority numbers based on the risk priority number threshold;
    updating the highlighting of the steps on the visually display graphical process tree based on the risk priority numbers of the updated risk priority numbers that exceed the risk priority number threshold;
    updating the risk management plan to mitigate risk based on the updated highlighted steps;
    adjusting the imaging workflow process in accordance with the updated risk management plan; and
    performing imaging examinations of patients using the adjusted imaging workflow process.

3. The method of claim 1, wherein the potential failure mode information for a step includes a severity value that indicates a severity of a potential failure mode, and further including computing a risk priority number for the step based on the severity value.

4. The method of claim 1, wherein the potential failure mode information for a step includes an occurrence value that indicates a likelihood of occurrence of the potential failure mode, and wherein calculating the at least one risk priority number for the step is based on the occurrence value.

5. The method of claim 1, wherein the potential failure mode information for a step includes a detectability value that indicates a detectability of a potential failure mode, and wherein calculating the at least one risk priority number for the step is based on the detectability value.

6. The method of claim 1, wherein the potential failure mode information for a step includes two or more of a severity value, an occurrence value and a detectability value, and wherein calculating the at least one risk priority number for the step is based on the two or more of the severity value, the occurrence value and the detectability value.

7. The method of claim 6, wherein all of the severity value, the occurrence value and the detectability value are user specified.

8. The method of claim 6, wherein at least one of the severity value, the occurrence value and the detectability value is initially unavailable and determined from the patient imaging performed according to the imaging workflow process using the risk management plan.

9. The method of claim 1, wherein the potential failure mode information includes a potential failure effect for each potential failure mode.

10. The method of claim 1, wherein the displayed potential failure mode information includes a potential failure cause for each potential failure mode.

11. The method of claim 1, wherein the displayed potential failure mode information indicates whether there is a current quality control process is in place for each potential failure mode.

12. The method of claim 1, wherein a first step includes at least two potential failure modes, and wherein the visually highlighting the displayed steps includes a first highlighting that indicates a risk priority number for one of the at least two potential failure modes that exceeds the risk priority number threshold and a second different highlighting that indicates risk priority numbers for the at least two potential failure modes that exceed the risk priority number threshold.

13. The method of claim 1, wherein the imaging workflow process tree describes temporal and physical relationships between the two or more of the steps of the imaging workflow.

14. A computing system, comprising:
    a graphical user interface;
    a memory device configured to store instructions, including a workflow supervisor module; and
    a processor that executes the instructions, which causes the processor to:
        display an imaging workflow process in the graphical user interface, the imaging workflow process comprising a plurality of steps;
        map the plurality of steps of the imaging workflow process into a pre-established standard imaging protocol or profile;
        display the mapped steps along with the imaging workflow process in the graphical user interface;
        process image examination information for failure mode information in accordance with the standard imaging protocol or profile, wherein the image examination information includes image examination for scans performed after implementation of a risk management plan for the imaging workflow process;
        calculate at least one risk metric for each step based on the failure mode information;
        evaluate the risk metric based on risk criteria;
        visually highlight steps of the mapped steps that satisfy the risk criteria in the graphical user interface;
        update the risk management plan to mitigate risk associated with the highlighted steps; and
        adjust the imaging workflow process in accordance with the updated risk management plan, wherein imaging examinations of patients are performed using the adjusted imaging workflow process.

15. The computing system of claim 14, wherein the risk metric is a risk priority number that quantifies a probability associated with a fault.

16. The computing system of claim 14, wherein the risk metric is a risk priority number computed from a failure severity value, a failure occurrence value and a failure detectability value.

17. The computing system of claim 14, wherein the risk metric is a hazard score.

18. A non-transitory computer readable medium encoded with computer executable instructions, which, when executed by a processor of a computer, cause the computer to:
construct and display a graphical process tree on a graphical user interface, for an imaging workflow process, with branches that correspond to steps for completing the imaging workflow process, wherein at least a subset of the steps are visually mapped into a pre-established standard imaging protocol or profile previously determined for the imaging workflow process;
calculate at least one risk priority number for each step based on input corresponding to potential failure modes;
process each risk priority number based on a risk priority number threshold;
identify steps having risk priority numbers that exceed the risk priority number threshold;
visually highlight the identified steps having the risk priority numbers that exceed the risk priority number threshold on the graphical user interface;
determine a risk management plan to mitigate risk associated with the highlighted steps;
update the at least one risk priority number based on image examination failures after implementing the risk management plan; and
update the risk management plan to mitigate risk based on the updated at least one risk priority number, and adjust the imaging workflow process in accordance with the updated risk management plan,
wherein imaging examinations of patients are performed using the adjusted imaging workflow process.

19. The method of claim 1, wherein visually highlighting steps of the visually displayed graphical process tree is based on grayscale coloring of the steps having risk priority numbers that exceed the risk priority number threshold.

20. The method of claim 19, wherein visually highlighting steps of the visually displayed graphical process tree comprises applying different shades of the grayscale coloring to respectively indicate a number of potential failure modes in the highlighted steps that cause the risk priority number to exceed the risk priority number threshold.

* * * * *